United States Patent [19]

Swift

[11] Patent Number: 5,329,060
[45] Date of Patent: Jul. 12, 1994

[54] INTEGRATED SELECTIVE ADSORPTION AND CRYSTALLIZATION PROCESS FOR PARA-XYLENE RECOVERY

[75] Inventor: John D. Swift, Hindhead Surrey, England

[73] Assignee: UOP, Des Plaines, Ill.

[21] Appl. No.: 41,375

[22] Filed: Apr. 1, 1993

[51] Int. Cl.[5] .................. C07C 7/00; C07C 7/14; C07C 7/12; C07C 5/22
[52] U.S. Cl. .................. 585/805; 585/815; 585/831; 585/479
[58] Field of Search .......... 585/805, 815, 831, 479

[56] References Cited

U.S. PATENT DOCUMENTS

| | | | |
|---|---|---|---|
| 3,729,523 | 4/1971 | Grandio, Jr. et al. | 260/674 A |
| 3,773,846 | 11/1973 | Berger | 585/805 |
| 3,813,452 | 5/1974 | Bieser | 585/805 |
| 3,835,198 | 9/1974 | Myers | 585/805 |
| 3,939,221 | 2/1976 | Pearce | 260/674 S A |

Primary Examiner—Anthony McFarlane
Assistant Examiner—Nhat D. Phan
Attorney, Agent, or Firm—Thomas K. McBride; John F. Spears, Jr.; Reginald K. Taylor

[57] ABSTRACT

The eutectic limit of para-xylene crystallization is overcome by enriching the concentration of para-xylene of the crystallization feed. This is accomplished by passing the crystallization feed stream through a selective adsorption zone to produce a para-xylene-enriched stream and a para-xylene-depleted stream. The para-xylene-depleted stream is passed to an isomerization zone to re-equilibrate the xylene mixture, thereby producing additional para-xylene. The para-xylene-enriched stream is passed to a crystallization zone to produce high purity para-xylene. The result is an increase in the overall para-xylene recovery.

22 Claims, 3 Drawing Sheets

P-XYLENE SEPARATION + CRYSTALLIZER MODEL

Figure 1: M-XYLENE SEPARATION + CRYSTALLIZER MODEL

Figure 2: P-XYLENE SEPARATION + CRYSTALLIZER MODEL

Figure 3: P-XYLENE SEPARATION + CRYSTALLIZER MODEL

INTEGRATED SELECTIVE ADSORPTION AND CRYSTALLIZATION PROCESS FOR PARA-XYLENE RECOVERY

FIELD OF THE INVENTION

The present invention relates to an improved process for the production of para-xylene. More specifically, the present invention involves the separation of a pure para-xylene product from a mixture of xylene isomers using selective adsorption and crystallization.

BACKGROUND OF THE INVENTION

Xylene isomers consist of para-xylene, meta-xylene, ortho-xylene and ethylbenzene. Para-xylene is used in the manufacture of terephthalic acid which in turn is subsequently employed in the manufacture of various synthetic fibers, such as polyester. Meta-xylene is used for the manufacture of insecticides, isophthalic acid or alkyd resins. Ortho-xylene can be used as material for plasticizers.

Xylenes are found in substantial quantities in coke oven light oils and certain virgin and reformed petroleum naphthas. In the past, it has been the practice in the separation of xylene isomers either to use chemical methods or to distill meta- and para-xylene, ethylbenzene and some paraffins from a fraction containing the xylene isomers, ethylbenzene, and paraffins. Typically, para-xylene and ortho-xylene are produced by recovery of these isomers from a mixed $C_8$ aromatic stream by means of fractionation, adsorption or crystallization.

The composition of the $C_8$ aromatic stream will vary depending on its source, but the total ortho- and para-xylene isomer content will be less than about 45 percent. Thus, a recovery process alone will not fully utilize the valuable feedstock. Under these circumstances, isomerization is useful. After depleting the $C_8$ aromatic feedstock of the valuable isomers (ortho- and para-xylene), the raffinate is generally sent to an isomerization unit. In the isomerization unit, an equilibrium xylene isomer ratio is reestablished, thus producing the desired isomers from the undesirable ones.

One method of producing a para-xylene product from a $C_8$ aromatic mixture is to first pass the $C_8$ mixture to a xylene column to remove heavies, for example, $C_9^-$ hydrocarbons. The overhead stream from the xylene column, containing predominantly para- and meta-xylene and ethylbenzene is passed to a crystallization unit. The crystallization unit is a separation process that takes advantage of the fact that for most xylene mixtures the melting point of para-xylene is higher than the other xylene isomers and crystallizes first. For example, para-xylene crystallizes at 13.3° C., meta-xylene at −47.9° C. and ortho-xylene −25.2° C. In the physical system of the three xylene isomers, there are two binary eutectics of importance, the para-xylene/meta-xylene and the para-xylene/ortho-xylene. As the para-xylene is crystallized from the mixture, the remaining mixture (mother liquor) composition approaches one of these eutectic binaries depending on the starting composition of the mixture. In commercial practice, para-xylene is crystallized so that the binary is only approached but not reached to avoid contaminating the crystal body with a mixture of crystals. This represents the eutectic limit to recovering para-xylene by crystallization. The crystallization unit produces a mother liquor which is recycled to the isomerization unit where the composition of the mother liquor is restored to the approximate concentration of the initial $C_8$ aromatic feedstock to form additional para-xylene.

The key disadvantage of crystallization is that the efficiency of the crystallization unit is restricted by the eutectic limit of the feed to the crystallization unit. A maximum extraction efficiency of about 65% is typical of commercial crystallization operations.

The eutectic limit problem of the crystallization process has been recognized in the $C_8$ aromatic separation art. In U.S. Pat. No. 3,939,221 (issued to Pearce), it is taught that the eutectic point of the crystallization unit could be overcome by passing the mother liquor generated by the crystallization unit through a selective adsorption unit prior to contacting the mother liquor with an isomerization catalyst to convert additional xylene isomers to para-xylene. The adsorption unit contains a crystalline aluminosilicate active for the selective adsorption of para-xylene from the mother liquor. Nowhere in the Pearce patent is there disclosed or suggested introducing a $C_8$ aromatic stream into a selective adsorption zone to provide a para-xylene-enriched stream for crystallization.

In U.S. Pat. No. 3,729,523, a process is disclosed for recovering high purity streams of all of the $C_8$ aromatic xylene isomers including ethylbenzene. The process passes a $C_8$ aromatic feed stream containing all of the xylene isomers through a selective adsorption unit to produce one stream containing meta- and ortho-xylene and another stream containing para-xylene and ethylbenzene. The stream containing the para-xylene and ethylbenzene is passed to a crystallization unit for removal of para-xylene and then to a first distillation zone for removal of ethylbenzene. The stream containing meta- and ortho-xylene is passed to a second distillation zone for removal of meta- and ortho-xylene. Also exiting this second distillation zone is a residual $C_8$ aromatic mixture that is sent to a low temperature isomerization zone (with toluene dilution) to form additional para-xylene.

There is a need for a cost effective method of producing high purity para-xylene from a $C_8$ aromatic mixture containing para-xylene, meta-xylene, ortho-xylene and ethylbenzene which overcomes the aforementioned eutectic limit for crystallization.

SUMMARY OF THE INVENTION

It has been discovered that the overall para-xylene recovery in a combination crystallization/isomerization process can be increased by ensuring that the stream passed to the isomerization zone contains the lowest para-xylene content. This increase is realized through the use of a selective adsorption zone that enriches the para-xylene feed to the crystallizer by rejecting meta- and ortho-xylene, ethylbenzene and other impurities to the isomerization zone. The selective adsorption zone can contain an adsorbent that is selective for the adsorption of meta-xylene and ortho-xylene or, in the alternative, selective for the adsorption of para-xylene. In the case where the adsorbent is selective for the adsorption of meta- and ortho-xylene, an extract rich in meta-xylene and ortho-xylene and depleted in para-xylene is rejected to the isomerization zone and a para-xylene-enriched raffinate is sent to the crystallization zone for recovery of para-xylene. In the case where the adsorbent is selective for the adsorption of para-xylene, a raffinate rich in meta-xylene and ortho-xylene and depleted in para-xylene is rejected to the isomerization zone and a para-xylene-enriched extract is sent to the crystallization zone for recovery of para-xylene.

By enriching the para-xylene concentration of the crystallization feed prior to passing the feed to the crystallization unit, overall para-xylene recovery in the crystallization unit can increase from approximately 65% to 85% and the eutectic limit on the efficiency is overcome.

The present invention is a process for the production of a substantially pure para-xylene isomer from a mixed xylene feedstock comprising ortho-, meta-and para-xylene isomers and ethylbenzene which process comprises the steps of: introducing at least a portion of the feedstock into a selective adsorption zone to produce a para-xylene-enriched stream and a para-xylene-depleted stream; passing at least a portion of the para-xylene-depleted stream to an isomerization zone containing an isomerization catalyst at conditions sufficient to produce an isomerate comprising an equilibrium xylene mixture; recycling at least a portion of the isomerate stream to the selective adsorption zone; passing at least a portion of the para-xylene-enriched stream to a crystallization zone to produce a para-xylene product stream and a mother liquor stream; and recycling at least a portion of the mother liquor to the selective adsorption zone.

In one embodiment, the present invention is a process for the production of a substantially pure para-xylene isomer from a mixed xylene feedstock comprising ortho-, meta- and para-xylene isomers and ethylbenzene which process comprises the steps of: introducing at least a portion of the feedstock into a selective adsorption zone to produce a para-xylene-enriched stream and a para-xylene-depleted stream; passing at least a portion of the para-xylene-depleted stream to an isomerization zone containing an isomerization catalyst at conditions sufficient to produce an isomerate comprising an equilibrium xylene mixture; recycling at least a portion of the isomerate stream to the selective adsorption zone; passing at least a portion of the para-xylene-enriched stream to a two-stage crystallization zone comprising a first stage crystallization zone which produces a first stage mother liquor and a second stage crystallization zone which produces a second stage mother liquor and a para-xylene product stream; and recycling at least a portion of the first stage mother liquor and admixing the first stage mother liquor with feed to the first stage crystallization zone.

In another embodiment, the present invention is a process for the production of a substantially pure para-xylene isomer from a mixed xylene feedstock comprising ortho-, meta- and para-xylene isomers and ethylbenzene which process comprises the steps of: introducing at least a portion of the feedstock into a selective adsorption zone to produce a para-xylene-enriched stream and a para-xylene-depleted stream; passing at least a portion of the para-xylene-depleted stream to an isomerization zone containing an isomerization catalyst at conditions sufficient to produce an isomerate comprising an equilibrium xylene mixture; recycling at least a portion of the isomerate stream to the selective adsorption zone; passing at least a portion of the para-xylene-enriched stream to a two-stage crystallization zone comprising a first stage crystallization zone which produces a first stage mother liquor and a second stage crystallization zone which produces a second stage mother liquor and a para-xylene product stream, the para-xylene-enriched stream being fed to the first stage crystallization zone; and recycling at least a portion of the first stage mother liquor and admixing the first stage mother liquor with feed to the first stage crystallization zone, and recycling at least a portion of the second stage mother liquor and admixing the second stage mother liquor with feed to the second stage crystallization zone.

In another embodiment, the present invention is a process for the production of a substantially pure para-xylene isomer from a mixed xylene feedstock comprising ortho-, meta- and para-xylene isomers and ethylbenzene which process comprises the steps of: introducing at least a portion of the feedstock into a selective adsorption zone to produce a para-xylene-enriched stream and a para-xylene-depleted stream; passing at least a portion of the para-xylene-depleted stream to an isomerization zone containing an isomerization catalyst at conditions sufficient to produce an isomerate comprising an equilibrium xylene mixture; recycling at least a portion of the isomerate stream to the selective adsorption zone; passing the para-xylene-enriched stream to a two-stage crystallization zone comprising a first stage crystallization zone which produces a first stage mother liquor and a second stage crystallization zone which produces a second stage mother liquor and a para-xylene product stream, the para-xylene-enriched stream being fed to the second stage crystallization zone; and recycling at least a portion of the second stage mother liquor and admixing the second stage mother liquor with feed to the second stage crystallization zone.

In another embodiment, the present invention is a process for the production of a substantially pure para-xylene isomer from a mixed xylene feedstock comprising ortho-, meta- and para-xylene isomers and ethylbenzene which process comprises the steps of: introducing at least a portion of the feedstock into a selective adsorption zone to produce a para-xylene-enriched stream and a para-xylene-depleted stream; passing at least a portion of the para-xylene-depleted stream to an isomerization zone containing an isomerization catalyst at conditions sufficient to produce an isomerate comprising an equilibrium xylene mixture; recycling at least a portion of the isomerate stream to the selective adsorption zone; passing the para-xylene-enriched stream to a two-stage crystallization zone comprising a first stage crystallization zone which produces a first stage mother liquor and a second stage crystallization zone which produces a second stage mother liquor and a para-xylene product stream, the para-xylene-enriched stream being fed to the second stage crystallization zone; recycling at least a portion of the second stage mother liquor and admixing the second stage mother liquor with feed to the second stage crystallization zone; and recycling at least a portion of the second stage mother liquor to the first stage crystallization zone.

DESCRIPTION OF THE PREFERRED EMBODIMENT

The $C_8$ aromatic hydrocarbon feedstock of the present invention comprises ortho-, meta-, para-xylene and ethylbenzene. The feedstock may also contain other hydrocarbon classes such as paraffins and naphthenes. Although other hydrocarbon classes may be present in the feedstock of the present invention, it is preferred that the mixture contain no substantial proportion of polymerizable or condensable hydrocarbons. In a preferred embodiment, the source of the $C_8$ aromatic-containing feedstock is a fraction derived from certain petroleum conversion products containing aromatic hydrocarbons and including fractions boiling within the range of about 120° C. to about 145° C. at atmospheric pressure. Suitable fractions utilizable as a feedstock in the present invention may be separated from gasoline produced by subjecting an appropriately boiling petroleum fraction to dehydrogenation as, for example, a hydroformed gasoline boiling range fraction containing naphthenic hydrocarbons. Such gasoline boiling range fractions of petroleum conversion products may be produced either thermally and/or produced in a catalyzed cracking, reforming, or hydroforming unit.

The feedstock of the present invention is introduced into a separation zone for the removal of $C_9^+$ hydrocarbons. In a preferred embodiment, this separation zone is a distillation column generally known as a xylene column. In one embodiment of the present invention, the xylene column is operated at conditions sufficient to separate out some or all of the ortho-xylene along with the $C_9^-$ hydrocarbons. The ortho-xylene can then be separated as an overhead stream in another distillation column known as an ortho-xylene column. In another embodiment, the xylene column is operated at conditions sufficient to separate out some or all of the $C_9^+$ hydrocarbons.

In accordance with the present invention, at least a portion of the effluent from the separation zone is passed to a selective adsorption zone. The selective adsorption zone contains an adsorbent which is either more selective for meta-xylene and ortho-xylene or more selective for para-xylene from the feed stream. In either case, two streams are produced. The first stream is a para-xylene-depleted stream and the second stream is a para-xylene-enriched stream. The para-xylene enriched stream can have a para-xylene concentration of about 20% to about 95% and is fed to a crystallization unit. The para-xylene depleted stream is rejected or passed to the isomerization zone.

In one embodiment of the present invention, the selective adsorption zone contains an adsorbent that is more selective for the adsorption of meta-xylene from the $C_8$ aromatic feed mixture. In this embodiment, the para-xylene-depleted stream is the meta-xylene extract produced from the selective adsorption zone and the para-xylene-enriched stream is the raffinate produced from the selective adsorption zone.

In another embodiment of the present invention, the selective adsorption zone contains an adsorbent that is more selective for the adsorption of para-xylene from the $C_8$ aromatic feed mixture. In this embodiment, the para-xylene-depleted stream is the raffinate produced from the selective adsorption zone and the para-xylene-enriched stream is the extract produced from the selective adsorption zone.

Adsorbents which can be used in the process of the present invention are generally referred to as crystalline aluminosilicate zeolites or molecular sieves and can comprise both the natural and synthetic aluminosilicates. A crystalline zeolitic aluminosilicate encompassed by the present invention for use as an adsorbent includes aluminosilicate cage structures in which alumina and silica tetrahedra are intimately connected with each other in an open three-dimensional crystalline network. The tetrahedra are cross-linked by the sharing of oxygen atoms with spaces between the tetrahedra occupied by water molecules prior to partial or total dehydration of this zeolite. The dehydration results with crystals interlaced with channels having molecular dimensions. Thus, the crystalline aluminosilicates are often referred to as molecular sieves. In a hydrated form the crystalline aluminosilicate is represented by the formula below:

$$M_{2/n}O:Al_2O_3:wSiO_2:yH_2O$$

where M is a cation which balances the electrovalence of the tetrahedra and is generally referred to as an exchangeable cation site, n represents the valence of the cation, w represents the moles of $SiO_2$, and y the moles of water. The cations may be any of a number of cations which will hereinafter be described in more detail.

Crystalline aluminosilicates which find use as the adsorbent in the process of the present invention possess relatively well defined pore structures. The exact type of aluminosilicate is generally referred to by the particular silica alumina ratio. Faujasites are commonly represented as being closely related to the type X and type Y aluminosilicates and are defined by the varying silica to alumina ratios.

The zeolite type X can be represented in terms of mole oxides as represented in the following equation:

$$0.9\pm0.2 M_{2/n}O:Al_2:2.5\pm0.5\ SiO_2:y\ H_2O$$

where M represents at least one cation having a valence of not more than 3, n represents the valence of M, and y is a value up to about 8 depending upon the identity of M and the degree of hydration of the crystalline. Zeolite X is described in U.S. Pat. No. 2,882,244.

The type Y zeolite can be represented in terms of mole ratio of oxides for the sodium form as represented in the following equation:

$$0.9\pm0.2\ NaO:Al_2O_3:wSiO_2:y\ H_2O$$

where w is a value greater than 3 up to about 8, and y may be any value up to about 9. The Y type zeolite is described in U.S. Pat. No. 3,130,007.

Adsorbents contemplated herein include not only the sodium form of the type Y zeolite but also crystalline materials contained from such a zeolite by partial or complete replacement of the sodium cations with other individual cations. Similarly, the type X zeolite also ion exchanges and is contemplated for use as an adsorbent process of this invention.

Cationic or base exchange methods are generally known to those familiar with the field of crystalline aluminosilicate production and are generally performed by contacting the zeolite with an aqueous solution of soluble salts of the cations desired to be exchanged in the sieves. A desired degree of cation exchange will take place before the sieves are removed from the aqueous solution and dried to a desired water content. It is contemplated that cationic exchange operations may take place using individual solutions of the desired cations to be placed on the molecular sieve or using an ion exchange solution containing mixtures to the cations desired to be placed on the crystalline aluminosilicate zeolite.

The cations which may be placed upon the crystalline aluminosilicate adsorbent include cations selected from the Group IA, Group IIA, and Group IB metals. The specific cations which would show a preferred selectivity for para-xylene with respect to ethylbenzene include lithium, sodium, potassium, rubidium, cesium, beryllium, magnesium, calcium, strontium, barium, silver, manganese, cadmium, and copper. Suitable cation pairs that can be used to separate para-xylene from a mixture containing para-xylene and meta-xylene are potassium and barium, potassium and beryllium, potassium and magnesium, potassium and rubidium, potassium and cesium, barium and rubidium, cesium and barium, and copper and potassium.

In instances in which the cation pairs comprise a Group IIA metal and a Group IA metal, the weight ratio of these two components upon the zeolite can vary from about 1:1 to about 80:1 depending upon the molecular weight of the Group IIA or Group IA metal. A particularly useful zeolite is one that contains barium and potassium cations having a weight ratio of barium to potassium of about 1:1 to about 40:1 and preferably in the range of about 1:1 to about 30:1. A ratio of about 5:1 to about 15:1 is an especially preferable range. The cations, when using Group IIA and Group IA metals, can occupy about 20 to 100% of the ion-exchangeable sites located upon the zeolite.

The cations which do not include the Group IIA and Group IA metals may be placed upon the zeolite in order that about 10 to 100% of the original cations present within the zeolite are replaced by these cations.

The desorbent used in the process of the present invention should be a material which is separable from the mixture that is fed to the solid adsorbent. Therefore, it is contemplated that a desorbent that is of a different boiling range than the feed mixture fed to the solid adsorbent be used in the separation process. The use of a desorbent of a different boiling range would allow fractionation or other separation methods to be used to separate the selectively adsorbed feed component as a relatively pure product stream and allow recovery of the desorbent for possible reuse in the process. Suitable desorbents include, but are not limited to, benzene, toluene, ethers, alcohols, cyclic dienes, and gaseous materials such as nitrogen, hydrogen, methane and ethane. In addition, desorbents which can be used in the process of this invention include the diethylbenzene isomers including paradiethylbenzene, meta-diethylbenzene and ortho-diethylbenzene along with small quantities of butylbenzenes which can be present in processes which reduce the diethylbenzene materials as products. It is preferable to use a desorbent which contains essentially para-diethylbenzene as a desorbing component of the desorbent. The typical ranges and concentrations of para-diethylbenzene when used as the sole diethylbenzene present in the desorbent can vary from 1 to 100% by volume of the total desorbent material passed into the adsorption process and preferably can be within the range of about 5 to about 60 volume % with an even more preferable range being about 30 to about 50 volume % of the total desorbent material. In instances in which the mixed diethylbenzenes are used as a component in a desorbent, they are present in an undiluted form and typically mixtures containing about 60 volume % meta-diethylbenzene, 7 volume % ortho-diethylbenzene, and about 26 volume % para-diethylbenzene along with about 7 volume % of butylbenzenes can make up a mixed diethylbenzene desorbent material.

The diluents which can be used with a desorbent material include saturated hydrocarbons including the paraffinic type hydrocarbons and cycloparaffins, and additionally the carbo-cyclic ring compounds. Typically, the diluent materials from the saturated paraffin group consist of the straight or branched-chain paraffins having from about 4 to about 20 carbon atoms per molecule and preferably having 4 to 10 carbon atoms per molecule. Cycloparaffins can include cyclohexane, cyclopentane, and branched derivatives thereof. Additional carbo-cyclic ring compounds including decahydronaphthalene and decahydronaphthalene derivatives containing branched chains can be utilized and are preferred as one diluent to be used in the process of this invention.

Adsorption conditions suitable for use in the present invention include the temperatures within the range of from 30° C. to 350° C. and preferably within the range of 40° C. to 250° C. Suitable adsorption zone pressures can range from atmospheric to 600 psig, preferably within the range of about atmospheric to about 400 psig. Both liquid phase and vapor phase operations can be used in the adsorption step and it is preferable to employ liquid phase operations because of the reduced temperature requirements and the decreasing opportunities for any type of side reaction to occur.

Suitable desorption conditions include substantially the same limitations as the adsorption conditions with the understanding that the desorption can take place with a reduction in pressure coupled with an increase in temperature. Preferably, desorption conditions and adsorption conditions take place at the same temperature in liquid phase operations.

In accordance with the present invention, the para-xylene-depleted stream is contacted with an isomerization catalyst in an isomerization zone at isomerization conditions sufficient to produce an isomerate comprising an equilibrium xylene mixture.

The isomerization catalyst can be any suitable isomerization catalyst known to those skilled in the art. The catalyst will typically comprise an acidic inorganic oxide support which has incorporated at least one metallic component.

With respect to the inorganic oxide binder utilized in the isomerization catalyst of the present invention, it is preferred that the binder be a porous, adsorptive, high surface area support having a surface area of about 25 m$^2$/g to about 500 m$^2$/g. The binder should also be uniform in composition and relatively refractory to the conditions utilized in the isomerization process of the present invention. Examples of suitable binders include alumina, silica, silica-alumina, zinc, titanium, zirconium, magnesia, thoria, chromia, boria, attapulgus clay, diatomaceous earth, Fuller's earth, kaolin, kieselguhr, and any mixtures thereof. The preferred binder is alumina. Suitable aluminas are the crystalline aluminas known as gamma, beta, and theta. The preferred alumina is gamma alumina. Preferred binders have an apparent bulk density of about 0.3 g/cc to about 0.8 g/cc and surface area characteristics such that the average pore diameter is about 20 to about 300 Angstroms and the pore volume is about 0.1 cc/g to about 1 cc/g.

With respect to the metallic component of the isomerization catalyst, the preferred metal is a Group VIII metal. Suitable Group VIII metals include platinum, palladium, rhodium, ruthenium, osmium, and iridium, preferably platinum. The Group VIII metal may exist within the final catalyst as an oxide, sulfide, halide, oxysulfide, or as an elemental metal, or as any combination thereof. The Group VIII metal component generally comprises about 0.01 wt. % to 2 about wt. % of the final component, preferably 0.05 to 1.0 wt. %.

The Group VIII metal compoenent may be incorporated into the isomerization catalyst of the present invention using any suitable means which results in the metal distribution disclosed herein. Suitable examples are ion exchange and impregnation. The preferred method of preparing the catalyst normally involves the use of a water-soluble decomposable compound of a Group VIII metal to impregnate a calcined zeolite/binder composite. For example, the Group VIII metal may be added to a calcined hydrogel by commingling the calcined composite with an aqueous solution of chloroplatinic or chloropalladic acid.

In a preferred embodiment, the isomerization catalyst of the present invention contains a lead component. The lead component may be incorporated into the catalytic composite in any suitable manner to effectively disperse this component on the individual moieties of the composite and to achieve the disclosed distribution of lead between the zeolite moiety and the binder moiety. A suitable method can include coprecipitation or cogelation with the inorganic oxide binder, ion-exchange with the inorganic oxide binder, or impregnation of the catalyst at any stage of precipitation. One preferred method of incorporating the lead component into the catalytic composite involves the addition of suitable soluble lead compounds such as lead nitrate, lead acetate, lead citrate, lead formate, and the like to the zeolite-containing hydrosol of the inorganic oxide, and then combining the hydrosol with a suitable gelling agent and dispersing the resulting mixture into an oil bath. After calcining the gelled hydrosol, there is obtained a binder material having a uniform dispersion of lead oxide in intimate combination principally with the inorganic binder.

Another preferred method of incorporating the lead component into the isomerization catalyst composite involves the use of a soluble, decomposable compound of lead to impregnate and uniformly disperse the lead on the composite.

In general, the lead component can be impregnated prior to, simultaneously with, or after the Group VIII metal is added to the carrier.

In another embodiment, the isomerization catalyst of the present invention contains a halogen component. The halogen is combined with the carrier material or with the other ingredients of the catalyst in the form of the corresponding halide. Suitable halogens include chlorine, iodine, bromine, or any mixture thereof, preferably fluorine and chlorine. The halogen may be added to the carrier material in any suitable manner known to those skilled in the art either during preparation of the carrier material or before or after the addition of the other components.

Regardless of how the isomerization catalyst components are combined with the porous carrier material, the catalyst composite will be dried at a temperature of from about 100° C. to about 320° C. for a period of about 2 to 24 hours. The desired composite is then calcined at a temperature of about 400° C. to about 600° C. in air at atmospheric conditions for a period of about 0.1 to 10 hours to convert the metallic compounds substantially to the oxide form. The resultant calcined composite may be subjected to a substantially water-free reduction step prior to its use in the conversion of hydrocarbons. The reducing agent, which is preferably hydrogen, contacts the catalyst at conditions including a temperature of about 200° C. to about 650° C. for a period of about 0.5 to 10 hours to reduce substantially all of the Group VIII metal components to the metallic state.

In a preferred embodiment, the isomerization catalyst of the present invention comprises a Group VIII metal, a lead component sufficient to amount to an atomic ratio of lead to a Group VIII metal from about 2:1 to about 10:1, from about 1 to 20 wt. % of a pentasil zeolite, and an inorganic binder, wherein from about 80 to 100 wt. % of the Group VIII metal and about 60 to 100 wt. % of the lead component are contained in the inorganic binder.

The isomerization catalyst of the present invention is disposed in an isomerization zone. The catalyst can be arranged in a fixed-bed system, a moving bed system, a fluidized bed system, or in a batch-type operation. In view of the danger of catalyst attrition loss and of operational advantages, it is preferred to use a fixed-bed system. In this system, a hydrogen gas and the feedstock are preheated by suitable heating means to the desired reaction temperature and then passed into an isomerization zone containing a fixed bed of catalyst. The isomerization conversion zone may be one or more separate reactors with suitable means therebetween to ensure that the desired isomerization temperature is maintained at the entrance to each zone. The reactants may be contacted with the catalyst in the upward, downward, or radial fashion. Further, the reactants may be in liquid phase, vapor phase, or vapor/liquid phase when contacting the catalyst.

Suitable isomerization conditions include a temperature of about 0° C. to about 600° C., preferably 350° C. to 500° C., a pressure of about 1 to 100 atmospheres, preferably 2 to 30 atmospheres, a hydrogen to hydrocarbon mole ratio of about 0.5:1 to about 15:1, and a liquid hourly space velocity of about 0.5 to 30 $hr^{-1}$.

In accordance with the present invention, at least a portion of the paraxylene-enriched stream is passed to the crystallization zone. Crystallization normally involves the removal of both sensible and latent heat to produce the crystalline paraxylene product. Indirect heat provided by heat exchangers, coils and jackets can be employed in the crystallization process of the present invention.

Generally crystallization can be divided into two stages. The first crystallization stage can have multiple crystallizers in series. In the first crystallizer stage, the refrigerant is kept at about −50° C. to about −70° C. Refrigeration is usually achieved by ethylene or evaporation. As the temperature drops, para-xylene crystals begin forming in the mother liquor. The temperature should be monitored and regulated to prevent crystallization of the other components in the mixture.

Feed generally enters the crystallizer near the top and exits near the bottom. Each crystallizer is usually equipped with scrapers that remove crystals adhering to the internal walls of the vessel. Further, crystallizer slurry can be recirculated to the crystallizer to classify the crystals within the crystallizer.

Effluent from the first stage crystallizer is passed to at least one first stage centrifuge. The first stage centrifuge operates to separate the mother liquor from the para-xylene crystals. In a preferred embodiment, a substantial amount of the mother liquor is recycled to the selective adsorption zone of the present invention. As used herein, substantial is defined as greater than about 50 mole %, preferably greater than about 65 mole %, most preferably greater than about 70 mole %.

Solid para-xylene crystals exiting the first stage centrifuge in the first stage crystallization zone can be melted and charged to a second stage crystallization zone. In the second stage, operations are similar to the first stage, except at a higher operating temperature of about $-10°$ C. Chilling can be provided by propane vaporization. The second stage generally produces larger-size crystals which increases separation efficiency.

The effluent exiting the second stage crystallizer can be passed to a second stage centrifuge. Solids separated in the second stage centrifuge usually have a higher degree of purity than the first stage.

Additional treatment of the second stage para-xylene crystals can include washing the para-xylene crystals with a variety of compounds including but not limited to para-xylene product, normal pentane, toluene, aqueous alcohols and aqueous salts to improve final product purity by removing adhering second stage mother liquor. After melting the crystals, it may be necessary to feed the resulting mixture to a fractionation column to separate the para-xylene product from the wash liquor.

The effect of para-xylene enrichment on the crystallization zone will depend on the degree of enrichment of the crystallization feed which could range from a small amount of enrichment (20 to 50 mole % para-xylene) to a large amount of enrichment (75 to 95 mole % para-xylene). In the embodiment where there is a large amount of enrichment, the crystallization zone can be reduced to a single stage which can be run at less severe conditions, for example, temperatures of $0°$ C. to $-10°$ C. In other words, the single stage crystallization zone can be run under second stage operating conditions. In this embodiment, the crystallization zone becomes limited only by the amount of solids that can readily flow in a stream rather than the previously-mentioned eutectic limit. Further in this embodiment, at least a portion of the mother liquor can be recycled and mixed with the crystallization feed to provide more liquor to carry additional recovered para-xylene. The mother liquor remaining after recycle can be returned to the selective adsorption zone to purge the non-para-xylene components.

In another embodiment of the present invention, a para-xylene-enriched stream having a para-xylene concentration of 75 to 95 mole % is passed to the second stage of the crystallizer rather than the first stage. In this embodiment, the crystallizer feed is blended with higher purity first stage product and some recycled second stage mother liquor. As a result, less second stage mother liquor can be recycled and is sent to the first stage as its primary feed. Accordingly, part of the para-xylene content can be recovered before the first stage mother liquor is recycled to the selective adsorption zone or the isomerization zone. The advantage of this approach is that the total aromatics being recycled to the selective adsorption unit are reduced (by the quantity of para-xylene recovered), thereby making the adsorption unit less costly. If sufficient para-xylene is recovered, the first stage mother liquor liquid can also be sent to the isomerization zone to reequilibrate the xylenes before separation. For higher enriched feed purities, the same approach is used and more second stage mother liquor can be recycled to the second stage feed, reducing the requirements of the first stage recovery. This flow scheme may also be applicable to the para-xylene feeds above a minimum concentration as the second stage feed should meet minimum purity requirements for adequate product quality.

Figure 1:
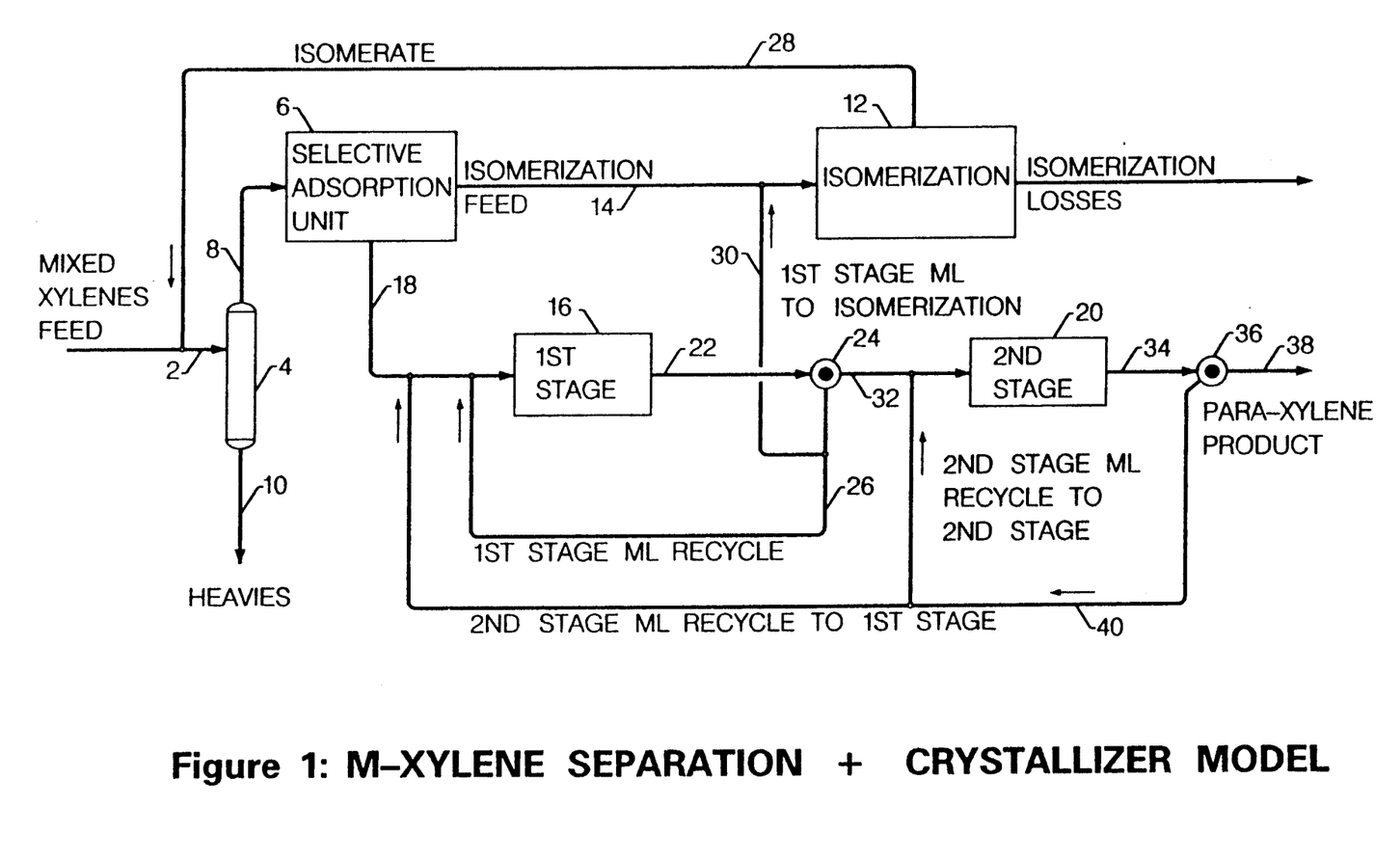
FIG. 1 is a schematic of an embodiment of the present invention wherein the selective adsorption zone contains an adsorbent which selectively adsorbs meta- and ortho-xylenes.

Referring to FIG. 1, a mixed xylene feedstock is combined with recycled isomerate 28 and passed to xylene column 4 through stream 2. Feed to selective adsorption unit 6 is taken overhead in stream 8 and $C_9^+$ hydrocarbons are taken from the bottom of column 4 via stream 10.

Selective adsorption unit 6 contains an adsorbent which is more selective for the adsorption of meta-xylene. In selective adsorption unit 6, a para-xylene-depleted extract comprising meta-xylene is produced along with a para-xylene-enriched raffinate. The para-xylene-depleted extract comprising meta-xylene is fed to isomerization zone 12 via line 14. The re-equilibrated isomerate exits isomerization zone 12 in line 28 and is recycled to xylene column 4 where any heavies, such as $C_9^+$ hydrocarbons, are removed.

The para-xylene-enriched raffinate is fed to first stage crystallization zone 16 via line 18. First stage crystallization zone 16 operates to produce crude para-xylene (para-xylene crystals in a mother liquor) which is sent to first stage centrifuge 24 for separation of the mother liquor from the para-xylene crystals. Exiting the first stage centrifuge 24 in stream 26 is mother liquor which is recycled and mixed with para-xylene feed to first stage crystallization zone 16. At least a portion of the mother liquor is passed to isomerization zone 12 via line 30.

The crystallized para-xylene from the first stage crystallization zone 16 is remelted and fed to second stage crystallization zone 20. In second stage crystallization zone 20, a portion of the contained para-xylene is recovered by crystallization. Effluent from second stage crystallization zone 20 exits second stage crystallization zone 20 via line 34 and is sent to second stage centrifuge 36. Second stage centrifuge 36 separates the second stage crystallization effluent into second stage mother liquor and purified para-xylene crystals. Second stage mother liquor is either recycled by line 40 and mixed with the feed to second stage crystallization zone 20 or recycled and mixed with feed to first stage crystallization zone 16. Crystallized para-xylene from second stage centrifuge 36 is remelted as stream 38. Wash liquor is added to second stage centrifuge 36 and collected separately from the mother liquor.

Figure 2:
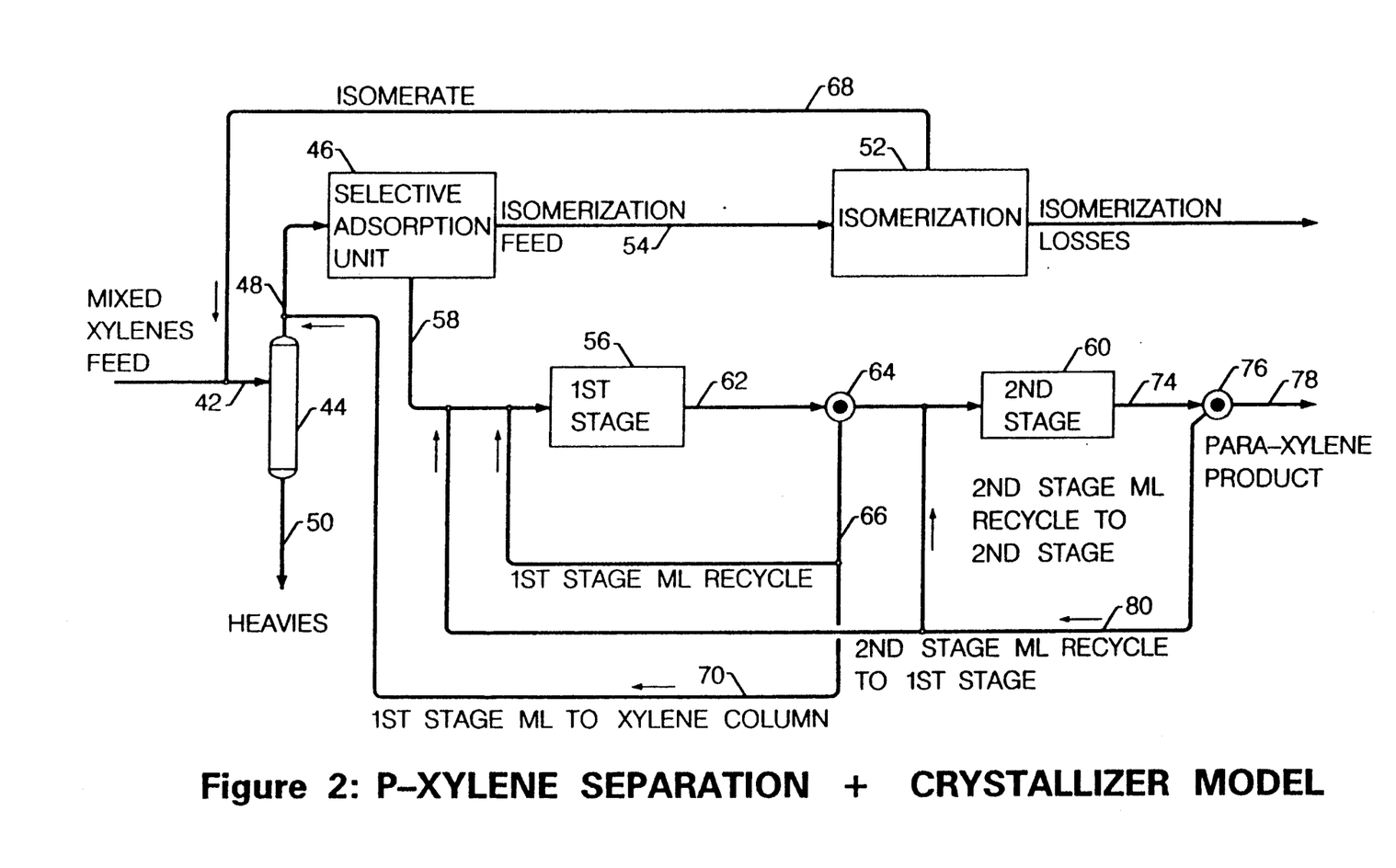
FIG. 2 is a schematic of an embodiment of the present invention wherein the selective adsorption zone contains an adsorbent which selectively adsorbs para-xylene.

Referring to FIG. 2, a mixed xylene feedstock is combined with recycled isomerate and passed to xylene column 44 through stream 42. Feed to selective adsorption unit 46 is taken overhead in stream 48 and $C_9^+$ hydrocarbons are taken from the bottom of column 44 via stream 50.

Selective adsorption unit 46 contains an adsorbent which is more selective for the adsorption of para-xylene. In selective adsorption unit 46, a para-xylene-depleted raffinate comprising meta-xylene and the other xylene isomers is produced along with a para-xylene-enriched extract. The para-xylene-depleted raffinate is fed to isomerization zone 52 via line 54. The re-equilibrated isomerate exits isomerization zone 52 in line 68 and is recycled to xylene column 44 where any heavies, such as $C_9^+$ hydrocarbons, are removed.

The para-xylene-enriched extract is fed to first stage crystallization zone 56 via line 58. First stage crystallization zone 56 operates to produce crude para-xylene (para-xylene crystals in a mother liquor) which is sent to first stage centrifuge 64 for separation of the mother liquor from the para-xylene crystals. Exiting first stage centrifuge 64 in stream 66 is a first stage mother liquor which is recycled and mixed with para-xylene feed to first stage crystallization zone 56. At least a portion of the first stage mother liquor is passed to selective adsorption unit 46 via line 70.

The crystallized para-xylene from first stage crystallization zone 56 is remelted and fed to second stage crystallization zone 60. In second stage crystallization zone 60, a portion of the contained para-xylene is recovered by crystallization. Effluent from second stage crystallization zone 60 exits second stage crystallization zone 60 via line 74 and is sent to second stage centrifuge 76. Mother liquor from second stage crystallization zone 60 is either recycled by line 80 and mixed with the feed to second stage crystallization zone 60 or recycled and mixed with feed to first stage crystallization zone 56. Crystallized para-xylene from second stage centrifuge 76 is remelted as stream 78. Wash liquor is added to second stage centrifuge 76 and collected separately from the mother liquor.

Figure 3:
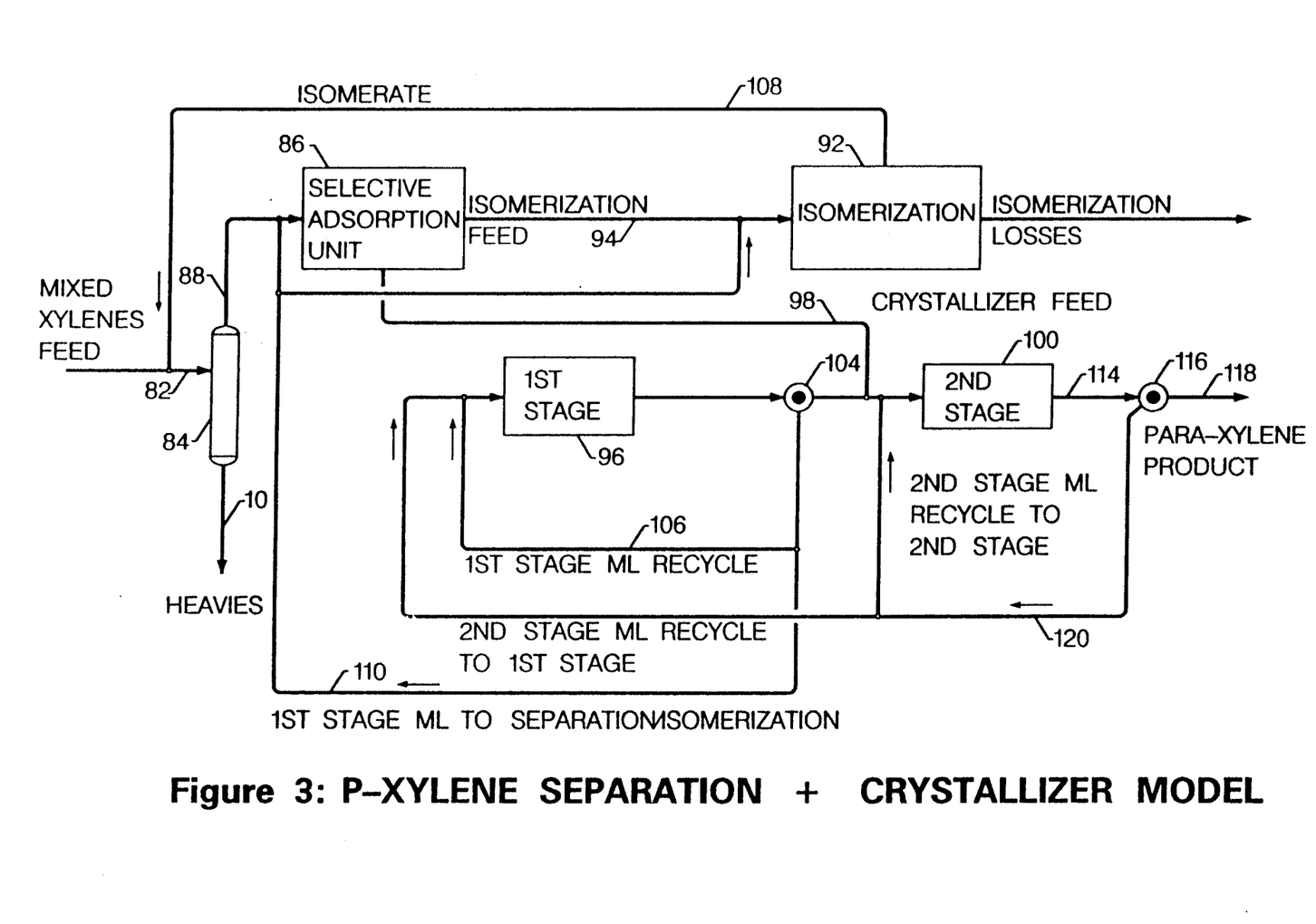
FIG. 3 is a schematic of an embodiment of the present invention wherein the selective adsorption zone contains an adsorbent which selectively adsorbs para-xylene. In contrast to FIG. 2, this schematic feeds the para-xylene-enriched stream to the second stage crystallization zone rather than the first stage crystallization zone.

Referring to FIG. 3. a mixed xylene feedstock is combined with recycled isomerate and passed to xylene column 84 through stream 82. Feed to selective adsorption unit 86 is taken overhead in stream 88 and $C_9^+$ hydrocarbons are taken from the bottom of column 84 via stream 90.

Selective adsorption unit 86 contains an adsorbent which is more selective for the adsorption of para-xylene. In selective adsorption unit 86, a para-xylene-depleted raffinate comprising meta-xylene and other xylene isomers is produced along with a para-xylene-enriched extract. The para-xylene-depleted raffinate is fed to isomerization zone 92 via line 94. The re-equilibrated isomerate exits isomerization zone 92 in line 108 and is recycled to xylene column 84 where any heavies, such as $C_9^+$ hydrocarbons, are removed.

The para-xylene-enriched extract is fed to second stage crystallization zone 100 via line 98. In second stage crystallization zone 100, a portion of the contained para-xylene is recovered by crystallization. Effluent from second stage crystallization zone 100 exits second stage crystallization zone 100 via line 114 and is sent to second stage centrifuge 116. At least a portion of the mother liquor from second stage crystallization zone 100 is recycled by line 120 and mixed with the feed to second stage crystallization zone 100. Product from second stage centrifuge 36 is recovered via line 118. Wash liquor is added to the second stage centrifuge 116 and collected separately from the mother liquor.

The remaining second stage mother liquor is recycled to first stage crystallization zone 96. First stage crystallization zone 96 operates to produce an effluent comprising para-xylene crystals in a first stage mother liquor. Effluent from the first stage crystallization zone is sent to first stage centrifuge 104 for separation of the first stage mother liquor from the para-xylene crystals. Exiting first stage centrifuge 104 in stream 106 is a first stage mother liquor which is recycled and mixed with recycled second stage mother liquor to first stage crystallization zone 96. At least a portion of the first stage mother liquor is passed to selective adsorption unit 86 via line 110.

EXAMPLES

In each of the following examples. a specific embodiment of the present invention is compared to a base case using computer simulations which are based on specific assumptions. The base case is a crystallizer/isomerization process without crystallization feed enrichment, i.e., without a selective adsorption zone. In example 1, the flow scheme presented in FIG. 1 is compared to the base case. In example 2, the flow scheme presented in FIG. 2 is compared to the base case. In example 3, the flow scheme presented in FIG. 3 is compared with the base case. It should be noted that the xylene isomerization operating conditions for all three of the examples are constant. Further, it is assumed that in the three examples isomerization includes the dealkylation of ethylbenzene.

EXAMPLE 1

In this example, a $C_8$ hydrocarbon feed stream containing 17.4 wt. % ethylbenzene, 18.2 wt. % para-xylene, 39.5 wt. % meta-xylene, 24.0 wt. % ortho-xylene and 0.9 wt. % $C_9^+$ heavies is passed through a selective adsorption zone containing adsorbent which is more selective for the adsorption of meta-xylene. In the selective adsorption zone, it is assumed that there is a recovery of 95% of feed meta-xylene to an extract containing 80 wt. % meta-xylene and 20 wt. % ortho-xylene. It is also assumed that there is no co-production of ortho-xylene from the complex.

The results are shown below in Table 1. As shown, the case that has the selective adsorption zone (meta-xylene) increased the para-xylene yield from 72.6% to 75.2% and the para-xylene recovery per pass from 63.9% to 85.9%.

TABLE 1

| Meta-xylene Separation scheme | | |
| --- | --- | --- |
| | Crystallizer Complex Base Case | Meta-Sep + Crystallizer Complex |
| Material Balance: Basis 100,000 MTA para-xylene 8,000 days on stream | | |
| | Flows kg/h | |
| Mixed Xylenes | 17,219 | 16,634 |
| Chem. Hydrogen (100%) | 125 | 111 |
| Para-xylene | 12,500 | 12,500 |
| Benzene | 2,007 | 1,935 |
| Toluene | 467 | 327 |
| Light Ends | 1,583 | 1,394 |
| Heavies | 787 | 589 |
| Para-xylene yield. % | 72.6 | 75.2 |
| Para-xylene recovery. % | 63.9 | 85.9 |

EXAMPLE 2

In this example, a $C_8$ hydrocarbon feed stream having the same composition as the feed used in Example 1 is passed through a selective adsorption zone containing adsorbent which is more selective for the adsorption of para-xylene. In the selective adsorption zone, it is assumed that there is a recovery of 95% of feed para-xylene to an extract containing 75 wt. % para-xylene, 15 wt. % ethylbenzene, 7.5 wt. % meta-xylene and 2.5 wt. % ortho-xylene. It is also assumed that there is no co-production of ortho-xylene from the complex.

The results are shown below in Table 2. As shown, the case that has the selective adsorption zone (para-xylene) increased the para-xylene yield from 72.6 to 75.2% and the para-xylene recovery per pass from 63.9% to an equivalent of 90.1%.

TABLE 2

Para-xylene Separation (option 1)

|  | Crystallizer Complex Base Case | Para-Sep + Crystallizer Complex Option 1 |
|---|---|---|
| Material Balance: Basis 100,000 MTA para-xylene 8,000 days on stream | | |
|  | Flows kg/h | |
| Mixed Xylenes | 17,219 | 16,560 |
| Chem. Hydrogen (100%) | 125 | 109 |
| Para-xylene | 12,500 | 12,500 |
| Benzene | 2,007 | 1,924 |
| Toluene | 467 | 309 |
| Light Ends | 1,583 | 1,368 |
| Heavies | 787 | 568 |
| Para-xylene yield, % | 72.6 | 75.5 |
| Para-xylene recovery, % | 63.9 | 45.7* |

*Equivalent to 90.1% overall Para-Sep + Crystallizer recovery.

EXAMPLE 3

In this example, a $C_8$ hydrocarbon feed steam having the same composition as the feed used in Example 1 is passed through a selective adsorption zone containing adsorbent which is more selective for the adsorption of para-xylene. In the selective adsorption zone, it is assumed that there is a recovery of 95% of feed para-xylene to an extract containing 75 wt. % para-xylene, 15 wt. % ethylbenzene, 7.5 wt. % meta-xylene and 2.5 wt. % ortho-xylene. It is also assumed that there is no co-production of ortho-xylene from the complex. This example can be contrasted with Example 2 in that in this example the para-xylene-enriched stream exiting the selective adsorption zone is fed to the second stage crystallization zone rather than being fed to the first crystallization zone as is the case with Example 2.

The results are shown below in Table 3. As shown, the case that has the selective adsorption zone (para-xylene) increased the para-xylene yield from 72.6 to 75.2% and the para-xylene recovery per pass from 63.9% to an equivalent of 90 wt. %.

TABLE 3

Para-xylene Separation (option 2)

|  | Crystallizer Complex Base Case | Para-Sep + Crystallizer Complex Option 2 |
|---|---|---|
| Material Balance: Basis 100,000 MTA para-xylene 8,000 days on stream | | |
|  | Flows kg/h | |
| Mixed Xylenes | 17,219 | 16,546 |
| Chem. Hydrogen (100%) | 125 | 108 |
| Para-xylene | 12,500 | 12,500 |
| Benzene | 2,007 | 1,918 |
| Toluene | 467 | 308 |
| Light Ends | 1,583 | 1,363 |
| Heavies | 787 | 566 |
| Para-xylene yield, % | 72.6 | 75.5 |
| Para-xylene recovery, % | 63.9 | 86.1* |

*Equivalent to 90.1% overall Para-Sep + Crystallizer recovery.

What is claimed is:

1. A process for the production of a substantially pure para-xylene isomer from a mixed xylene feedstock comprising ortho-, meta- and para-xylene isomers and ethylbenzene which process comprises the steps of:
   (a) introducing at least a portion of said feedstock into a selective adsorption zone to produce a para-xylene-enriched stream and a para-xylene-depleted stream;
   (b) passing at least a portion of said para-xylene-depleted stream to an isomerization zone containing an isomerization catalyst at conditions sufficient to produce an isomerate comprising an equilibrium xylene mixture;
   (c) recycling at least a portion of said isomerate stream to said selective adsorption zone;
   (d) passing at least a portion of said para-xylene-enriched stream to a crystallization zone to produce a para-xylene product stream and a mother liquor stream; and
   (e) recycling at least a portion of said mother liquor to said selective adsorption zone.

2. The process of claim 1 wherein a substantial portion of said mother liquor stream is recycled to said selective adsorption zone.

3. The process of claim 1 wherein said crystallization zone comprises a single stage operating at a temperature of about 0° C. to about −10° C.

4. The process of claim 1 wherein said crystallization zone comprises a first stage and second stage process, said first stage producing a first stage mother liquor and operating a temperature of about −50° C. to about −75° C. and said second stage producing a second stage mother liquor and operating a temperature of about 0° C. to about −10° C.

5. The process of claim 4 wherein at least a portion of said first stage liquor is recycled and admixed with feed to said first stage crystallization zone.

6. The process of claim 4 wherein at least a portion of said first stage liquor is recycled to said selective adsorption zone.

7. The process of claim 4 wherein at least a portion of said second stage liquor is recycled and admixed with feed to said second stage crystallization zone.

8. The process of claim 4 wherein at least a portion of said second stage liquor is recycled and admixed with feed to said first stage crystallization zone.

9. The process of claim 4 wherein at least a portion of said paraxylene-enriched stream is fed to said second stage crystallization zone.

10. The process of claim 9 wherein at least a portion of said first stage mother liquor is recycled and admixed with feed to said first stage crystallization zone.

11. The process of claim 9 wherein at least a portion of said first stage mother liquor is recycled to said selective adsorption zone.

12. The process of claim 9 wherein at least a portion of said second stage mother liquor is recycled and admixed with feed to said second stage crystallization zone.

13. The process of claim 9 wherein at least a portion of said second stage mother liquor is recycled and admixed with feed to said first stage crystallization zone.

14. The process of claim 1 wherein said adsorbent comprises a component active for the preferential adsorption of para-xylene.

15. The process of claim 1 wherein said adsorbent comprises a component active for the preferential adsorption of meta-xylene.

16. The process of claim 1 wherein said xylene feedstock is passed to a xylene column to produce a xylene column effluent stream comprising $C_9^+$ hydrocarbons prior to introducing said feedstock to said selective adsorption zone.

17. The process of claim 16 further comprising operating said xylene column at conditions sufficient to produce a xylene column effluent stream that comprises $C_9^+$ hydrocarbons and ortho-xylene.

18. The process of claim 17 further comprising passing said xylene column effluent stream to a ortho-xylene column to produce an ortho-xylene product stream.

19. A process for the production of a substantially pure para-xylene isomer from a mixed xylene feedstock comprising ortho-, meta- and para-xylene isomers and ethylbenzene which process comprises the steps of:
   (a) introducing at least a portion of said feedstock into a selective adsorption zone to produce a para-xylene-enriched stream and a para-xylene-depleted stream;
   (b) passing at least a portion of said para-xylene-depleted stream to an isomerization zone containing an isomerization catalyst at conditions sufficient to produce an isomerate comprising an equilibrium xylene mixture;
   (c) recycling at least a portion of said isomerate stream to said selective adsorption zone;
   (d) passing at least a portion of said para-xylene-enriched stream to a two-stage crystallization zone comprising a first stage crystallization zone which produces a first stage mother liquor and a second stage crystallization zone which produces a second stage mother liquor and a para-xylene product stream;
   (e) recycling at least a portion of said first stage mother liquor and admixing said first stage mother liquor with feed to said first stage crystallization zone; and
   (f) recycling at least a portion of said second stage mother liquor and admixing the second stage mother liquor with feed to the second stage crystallization zone.

20. A process for the production of a substantially pure para-xylene isomer from a mixed xylene feedstock comprising ortho-, meta- and para-xylene isomers and ethylbenzene which process comprises the steps of:
   (a) introducing at least a portion of said feedstock into a selective adsorption zone to produce a para-xylene-enriched stream and a para-xylene-depleted stream;
   (b) passing at least a portion of said para-xylene-depleted stream to an isomerization zone containing an isomerization catalyst at conditions sufficient to produce an isomerate comprising an equilibrium xylene mixture;
   (c) recycling at least a portion of said isomerate stream to said selective adsorption zone;
   (d) passing at least a portion of said para-xylene-enriched stream to a two-stage crystallization zone comprising a first stage crystallization zone which produces a first stage mother liquor and a second stage crystallization zone which produces a second stage mother liquor and a para-xylene product stream; and
   (e) recycling at least a portion of said second stage mother liquor and admixing said second stage mother liquor with feed to said second stage crystallization zone.

21. A process for the production of a substantially pure para-xylene isomer from a mixed xylene feedstock comprising ortho-, meta- and para-xylene isomers which process comprises the steps of:
   (a) introducing at least a portion of said feedstock into a selective adsorption zone to produce a para-xylene-enriched stream and a para-xylene-depleted stream;
   (b) passing at least a portion of said para-xylene-depleted stream to an isomerization zone containing an isomerization catalyst at conditions sufficient to produce an isomerate comprising an equilibrium xylene mixture;
   (c) recycling at least a portion of said isomerate stream to said selective adsorption zone;
   (d) passing said para-xylene-enriched stream to a two-stage crystallization zone comprising a first stage crystallization zone which produces a first stage mother liquor and a second stage crystallization zone which produces a second stage mother liquor and a para-xylene product stream, said para-xylene-enriched stream being fed to said second stage crystallization zone; and
   (e) recycling at least a portion of said second stage mother liquor and admixing said second stage mother liquor with feed to said second stage crystallization zone.

22. A process for the production of a substantially pure para-xylene isomer from a mixed xylene feedstock comprising ortho-, meta- and para-xylene isomers and ethylbenzene which process comprises the steps of:
   (a) introducing at least a portion of the feedstock into a selective adsorption zone to produce a para-xylene-enriched stream and a para-xylene-depleted stream;
   (b) passing at least a portion of the para-xylene-depleted stream to an isomerization zone containing an isomerization catalyst at conditions sufficient to produce an isomerate comprising an equilibrium xylene mixture; recycling at least a portion of the isomerate stream to the selective adsorption zone;
   (c) passing the para-xylene-enriched stream to a two-stage crystallization zone comprising a first stage crystallization zone which produces a first stage mother liquor and a second stage crystallization zone which produces a second stage mother liquor and a para-xylene product stream, the para-xylene-enriched stream being fed to the second stage crystallization zone;
   (d) recycling at least a portion of the second stage mother liquor and admixing the second stage mother liquor with feed to the second stage crystallization zone; and
   (e) recycling at least a portion of the second stage mother liquor to the first stage crystallization zone.

* * * * *